US010017830B2

(12) United States Patent
Wang et al.

(10) Patent No.: US 10,017,830 B2
(45) Date of Patent: Jul. 10, 2018

(54) OLIGONUCLEOTIDE PROBES, KIT CONTAINING THE SAME AND METHOD FOR PATHOTYPING OF H5 AVIAN INFLUENZA VIRUSES

(71) Applicant: National Taiwan University, Taipei (TW)

(72) Inventors: Lih-Chiann Wang, Taipei (TW); Chien-Hao Huang, Taipei (TW); Ching-Ho Wang, Taipei (TW)

(73) Assignee: National Taiwan University, Taipei (TW)

( * ) Notice: Subject to any disclaimer, the term of this patent is extended or adjusted under 35 U.S.C. 154(b) by 581 days.

(21) Appl. No.: 14/286,402

(22) Filed: May 23, 2014

(65) Prior Publication Data

US 2015/0337398 A1 Nov. 26, 2015

(51) Int. Cl.
*C07H 21/04* (2006.01)
*C12Q 1/68* (2018.01)
*C12Q 1/70* (2006.01)

(52) U.S. Cl.
CPC .................................... *C12Q 1/701* (2013.01)

(58) Field of Classification Search
None
See application file for complete search history.

(56) References Cited

U.S. PATENT DOCUMENTS 6,582,908 B2 * 6/2003 Fodor .................. B01J 19/0046 435/288.3
2010/0048423 A1 * 2/2010 Pan ........................ C12Q 1/701 506/16
2014/0080726 A1 * 3/2014 Prakash ............... C12Q 1/6816 506/9

OTHER PUBLICATIONS

NEB catalog (1998/1999 p. 121).*
Hoffmann, Bernd et al., Rapid and Highly Sensitive Pathotyping of Avian Influenza a H5N1 Virus by Using Real-Time Reverse Transcription-PCR, *J. Clin. Microbiol.* Feb. 2007, vol. 45, No. 2, pp. 600-603
Leijon, Mikael et al., Rapid PCR-Based Molecular Pathotyping of H5 and H7 Avian Influenza Viruses, Journal of Clinical Microbiology, Nov. 2011, vol. 49, No. 11, pp. 3860-3873.

* cited by examiner

*Primary Examiner* — Amanda Marie Haney
(74) *Attorney, Agent, or Firm* — Muncy, Geissler, Olds & Lowe, P.C.

(57) ABSTRACT

The present invention provides a group of specific probes directed to cleavage site of hemagglutinin precursor protein of avian influenza virus subtypes H5, and provides a method for rapid pathotyping of H5 avian influenza virus. The present invention further provides a kit containing the probes and the kit is easy-to-use, low-cost, high sensitivity, enabled the molecular pathotyping of H5 viruses by a simpler and faster means that conventional methods.

10 Claims, 2 Drawing Sheets

(A)

(B)

```
                              SEQUENCE LISTING

<160> NUMBER OF SEQ ID NOS: 51

<210> SEQ ID NO 1
<211> LENGTH: 22
<212> TYPE: DNA
<213> ORGANISM: Artificial Sequence
<220> FEATURE:
<223> OTHER INFORMATION: probe
<220> FEATURE:
<221> NAME/KEY: misc_feature
<222> LOCATION: (1)..(22)

<400> SEQUENCE: 1

gagtgyccma artaygtsaa at                                               22


<210> SEQ ID NO 2
<211> LENGTH: 22
<212> TYPE: DNA
<213> ORGANISM: Artificial Sequence
<220> FEATURE:
<223> OTHER INFORMATION: probe
<220> FEATURE:
<221> NAME/KEY: misc_feature
<222> LOCATION: (1)..(22)

<400> SEQUENCE: 2

gaatgyccca rataygtgaa at                                               22


<210> SEQ ID NO 3
<211> LENGTH: 18
<212> TYPE: DNA
<213> ORGANISM: Artificial Sequence
<220> FEATURE:
<223> OTHER INFORMATION: probe
<220> FEATURE:
<221> NAME/KEY: misc_feature
<222> LOCATION: (1)..(18)

<400> SEQUENCE: 3
```

ccycaratag aracaagr 18

<210> SEQ ID NO 4
<211> LENGTH: 18
<212> TYPE: DNA
<213> ORGANISM: Artificial Sequence
<220> FEATURE:
<223> OTHER INFORMATION: probe
<220> FEATURE:
<221> NAME/KEY: misc_feature
<222> LOCATION: (1)..(18)

<400> SEQUENCE: 4
ccycarggag aracaagr 18

<210> SEQ ID NO 5
<211> LENGTH: 18
<212> TYPE: DNA
<213> ORGANISM: Artificial Sequence
<220> FEATURE:
<223> OTHER INFORMATION: probe
<220> FEATURE:
<221> NAME/KEY: misc_feature
<222> LOCATION: (1)..(18)

<400> SEQUENCE: 5
ccycaragag aracraga 18

<210> SEQ ID NO 6
<211> LENGTH: 18
<212> TYPE: DNA
<213> ORGANISM: Artificial Sequence
<220> FEATURE:
<223> OTHER INFORMATION: probe
<220> FEATURE:
<221> NAME/KEY: misc_feature
<222> LOCATION: (1)..(18)

<400> SEQUENCE: 6
ccycaaaarg aaacaara 18

<210> SEQ ID NO 7
<211> LENGTH: 18
<212> TYPE: DNA
<213> ORGANISM: Artificial Sequence
<220> FEATURE:
<223> OTHER INFORMATION: probe
<220> FEATURE:
<221> NAME/KEY: misc_feature
<222> LOCATION: (1)..(18)

<400> SEQUENCE: 7
ccymaaarag aarcaaga 18

<210> SEQ ID NO 8
<211> LENGTH: 18
<212> TYPE: DNA
<213> ORGANISM: Artificial Sequence
<220> FEATURE:
<223> OTHER INFORMATION: probe
<220> FEATURE:
<221> NAME/KEY: misc_feature
<222> LOCATION: (1)..(18)

<400> SEQUENCE: 8
ccycaaagar ccacaara 18

<210> SEQ ID NO 9

<211> LENGTH: 18
<212> TYPE: DNA
<213> ORGANISM: Artificial Sequence
<220> FEATURE:
<223> OTHER INFORMATION: probe
<220> FEATURE:
<221> NAME/KEY: misc_feature
<222> LOCATION: (1)..(18)

<400> SEQUENCE: 9
ccagagaatc caaagccc 18

<210> SEQ ID NO 10
<211> LENGTH: 18
<212> TYPE: DNA
<213> ORGANISM: Artificial Sequence
<220> FEATURE:
<223> OTHER INFORMATION: probe
<220> FEATURE:
<221> NAME/KEY: misc_feature
<222> LOCATION: (1)..(18)

<400> SEQUENCE: 10
mgagaaaaaa gaggmcta 18

<210> SEQ ID NO 11
<211> LENGTH: 18
<212> TYPE: DNA
<213> ORGANISM: Artificial Sequence
<220> FEATURE:
<223> OTHER INFORMATION: probe
<220> FEATURE:
<221> NAME/KEY: misc_feature
<222> LOCATION: (1)..(18)

<400> SEQUENCE: 11
ccycaaagaa aaacaaga 18

<210> SEQ ID NO 12
<211> LENGTH: 18
<212> TYPE: DNA
<213> ORGANISM: Artificial Sequence
<220> FEATURE:
<223> OTHER INFORMATION: probe
<220> FEATURE:
<221> NAME/KEY: misc_feature
<222> LOCATION: (1)..(18)

<400> SEQUENCE: 12
ccycaaagra rraaaaga 18

<210> SEQ ID NO 13
<211> LENGTH: 18
<212> TYPE: DNA
<213> ORGANISM: Artificial Sequence
<220> FEATURE:
<223> OTHER INFORMATION: probe
<220> FEATURE:
<221> NAME/KEY: misc_feature
<222> LOCATION: (1)..(18)

<400> SEQUENCE: 13
ccycagaaga araagaga 18

<210> SEQ ID NO 14
<211> LENGTH: 29
<212> TYPE: DNA
<213> ORGANISM: Artificial Sequence
<220> FEATURE:

-continued

<223> OTHER INFORMATION: probe
<220> FEATURE:
<221> NAME/KEY: misc_feature
<222> LOCATION: (1)..(29)

<400> SEQUENCE: 14
atgaagcatg tcagggcttg gatacctcg 29

<210> SEQ ID NO 15
<211> LENGTH: 25
<212> TYPE: DNA
<213> ORGANISM: Artificial Sequence
<220> FEATURE:
<223> OTHER INFORMATION: primer
<220> FEATURE:
<221> NAME/KEY: misc_feature
<222> LOCATION: (1)..(25)
<220> FEATURE:
<221> NAME/KEY: misc_feature
<222> LOCATION: (9)..(9)
<223> OTHER INFORMATION: n is a, c, g, or t

<400> SEQUENCE: 15
atwgctccng aatatgcatw waara 25

<210> SEQ ID NO 16
<211> LENGTH: 27
<212> TYPE: DNA
<213> ORGANISM: Artificial Sequence
<220> FEATURE:
<223> OTHER INFORMATION: primer
<220> FEATURE:
<221> NAME/KEY: misc_feature
<222> LOCATION: (1)..(27)

<400> SEQUENCE: 16
tcraaytgar tgttcatttt rtcaatg 27

<210> SEQ ID NO 17
<211> LENGTH: 116
<212> TYPE: DNA
<213> ORGANISM: Artificial Sequence
<220> FEATURE:
<223> OTHER INFORMATION: artificial oligonucleotide spanning the CS
region of AIV
<220> FEATURE:
<221> NAME/KEY: misc_feature
<222> LOCATION: (1)..(116)

<400> SEQUENCE: 17
ccccttacca ttggagagtg tcccaaatat gtcaaatcaa ataaactggt ccttgcaaca 60
ggaccgagga acgtgcctca aagaagaaaa aaaagaggtc tgtttggagc aaaagc 116

<210> SEQ ID NO 18
<211> LENGTH: 120
<212> TYPE: DNA
<213> ORGANISM: Artificial Sequence
<220> FEATURE:
<223> OTHER INFORMATION: artificial oligonucleotide spanning the CS
region of AIV
<220> FEATURE:
<221> NAME/KEY: misc_feature
<222> LOCATION: (1)..(120)

<400> SEQUENCE: 18
tccttttact attggggagt gccccaagta tgtcaaatcg aaaaaactag ttcttgcaac 60
agggctaaga aacgtacccc aaagaaaaag aaaaacaaga ggcctatttg gagcaatagc 120

<210> SEQ ID NO 19
<211> LENGTH: 122
<212> TYPE: DNA
<213> ORGANISM: Artificial Sequence
<220> FEATURE:
<223> OTHER INFORMATION: artificial oligonucleotide spanning the CS region of AIV
<220> FEATURE:
<221> NAME/KEY: misc_feature
<222> LOCATION: (1)..(122)

<400> SEQUENCE: 19
ctctcaccat cggggaatgc cccaaatatg tgaaatcaaa cagattagtc ctcgcgactg 60
gactcagaaa tgccccccaa atagagggaa gaagaagaaa aagaggacta tttggagcca 120
ta 122

<210> SEQ ID NO 20
<211> LENGTH: 118
<212> TYPE: DNA
<213> ORGANISM: Artificial Sequence
<220> FEATURE:
<223> OTHER INFORMATION: artificial oligonucleotide spanning the CS region of AIV
<220> FEATURE:
<221> NAME/KEY: misc_feature
<222> LOCATION: (1)..(118)

<400> SEQUENCE: 20
ctctcaccat tggggaatgc cccagatacg tgaaatcaga tagattagtc cttgcgactg 60
gactcaggaa tgtccctcaa agaagaagaa aaaaaagagg actatttggg gctatagc 118

<210> SEQ ID NO 21
<211> LENGTH: 121
<212> TYPE: DNA
<213> ORGANISM: Artificial Sequence
<220> FEATURE:
<223> OTHER INFORMATION: artificial oligonucleotide spanning the CS region of AIV
<220> FEATURE:
<221> NAME/KEY: misc_feature
<222> LOCATION: (1)..(121)

<400> SEQUENCE: 21
ctctcaccat cggggaatgc cccaaatatg tgaaatcaaa cagattagtc cttgcgactg 60
ggctcagaaa tagccctcaa agagagagaa gaaaaaagag aggattattt ggagctatag 120
c 121

<210> SEQ ID NO 22
<211> LENGTH: 121
<212> TYPE: DNA
<213> ORGANISM: Artificial Sequence
<220> FEATURE:
<223> OTHER INFORMATION: artificial oligonucleotide spanning the CS region of AIV
<220> FEATURE:
<221> NAME/KEY: misc_feature
<222> LOCATION: (1)..(121)

<400> SEQUENCE: 22
ctctcaccat cggggaatgc cccaaatatg tgaaatcaaa caaattggtc cttgcgactg 60
ggctcagaaa tagtcctcta agagaaagaa gaagaaaaag aggactattt ggagctatag 120
c 121

<210> SEQ ID NO 23
<211> LENGTH: 124
<212> TYPE: DNA
<213> ORGANISM: Artificial Sequence
<220> FEATURE:
<223> OTHER INFORMATION: artificial oligonucleotide spanning the CS region of AIV
<220> FEATURE:
<221> NAME/KEY: misc_feature
<222> LOCATION: (1)..(124)

<400> SEQUENCE: 23
ctctcaccat cggggaatgc cccaaatatg tgaaatcaaa cagattagtc cttgcaacag 60
gactcagaaa cagccctcaa agagagagca gaagaaaaaa gagaggacta tttggagcta 120
tagc 124

<210> SEQ ID NO 24
<211> LENGTH: 124
<212> TYPE: DNA
<213> ORGANISM: Artificial Sequence
<220> FEATURE:
<223> OTHER INFORMATION: artificial oligonucleotide spanning the CS region of AIV
<220> FEATURE:
<221> NAME/KEY: misc_feature
<222> LOCATION: (1)..(124)

<400> SEQUENCE: 24
ctctcaccat cggagaatgt cccaaatatg tgaaatcaaa caaattagtc cttgcgactg 60
ggctcagaaa tagtcctcaa agagagagaa gaagaagaaa aagaggactg tttggagcta 120
tagc 124

<210> SEQ ID NO 25
<211> LENGTH: 124
<212> TYPE: DNA
<213> ORGANISM: Artificial Sequence
<220> FEATURE:
<223> OTHER INFORMATION: artificial oligonucleotide spanning the CS region of AIV
<220> FEATURE:
<221> NAME/KEY: misc_feature
<222> LOCATION: (1)..(124)

<400> SEQUENCE: 25
ctctcaccat cggggaatgc cccaaatatg tgaaatcaaa cagattagtc cttgcgactg 60
ggctcagaaa tagccctcaa agagagagaa gaagaaaaaa gagaggacta tttggagcta 120
tagc 124

<210> SEQ ID NO 26
<211> LENGTH: 10
<212> TYPE: PRT
<213> ORGANISM: Artificial Sequence
<220> FEATURE:
<223> OTHER INFORMATION: corresponding amino acids around the CS in AIV
<220> FEATURE:
<221> NAME/KEY: MISC_FEATURE
<222> LOCATION: (1)..(10)

<400> SEQUENCE: 26

Pro Gln Arg Arg Lys Lys Arg Gly Leu Phe
1               5                   10

<210> SEQ ID NO 27
<211> LENGTH: 11
<212> TYPE: PRT

-continued

<213> ORGANISM: Artificial Sequence
<220> FEATURE:
<223> OTHER INFORMATION: corresponding amino acids around the CS in AIV
<220> FEATURE:
<221> NAME/KEY: MISC_FEATURE
<222> LOCATION: (1)..(11)

<400> SEQUENCE: 27

Pro Gln Arg Lys Arg Lys Thr Arg Gly Leu Phe
1               5                   10

<210> SEQ ID NO 28
<211> LENGTH: 13
<212> TYPE: PRT
<213> ORGANISM: Artificial Sequence
<220> FEATURE:
<223> OTHER INFORMATION: corresponding amino acids around the CS in AIV
<220> FEATURE:
<221> NAME/KEY: MISC_FEATURE
<222> LOCATION: (1)..(13)

<400> SEQUENCE: 28

Pro Gln Ile Glu Gly Arg Arg Arg Lys Arg Gly Leu Phe
1               5                   10

<210> SEQ ID NO 29
<211> LENGTH: 11
<212> TYPE: PRT
<213> ORGANISM: Artificial Sequence
<220> FEATURE:
<223> OTHER INFORMATION: corresponding amino acids around the CS in AIV
<220> FEATURE:
<221> NAME/KEY: MISC_FEATURE
<222> LOCATION: (1)..(11)

<400> SEQUENCE: 29

Pro Gln Arg Arg Arg Lys Lys Arg Gly Leu Phe
1               5                   10

<210> SEQ ID NO 30
<211> LENGTH: 12
<212> TYPE: PRT
<213> ORGANISM: Artificial Sequence
<220> FEATURE:
<223> OTHER INFORMATION: corresponding amino acids around the CS in AIV
<220> FEATURE:
<221> NAME/KEY: MISC_FEATURE
<222> LOCATION: (1)..(12)

<400> SEQUENCE: 30

Pro Gln Arg Glu Arg Arg Lys Lys Arg Gly Leu Phe
1               5                   10

<210> SEQ ID NO 31
<211> LENGTH: 12
<212> TYPE: PRT
<213> ORGANISM: Artificial Sequence
<220> FEATURE:
<223> OTHER INFORMATION: corresponding amino acids around the CS in AIV
<220> FEATURE:
<221> NAME/KEY: MISC_FEATURE
<222> LOCATION: (1)..(12)

<400> SEQUENCE: 31

Pro Leu Arg Glu Arg Arg Arg Lys Arg Gly Leu Phe
1               5                   10

<210> SEQ ID NO 32
<211> LENGTH: 13

-continued

<212> TYPE: PRT
<213> ORGANISM: Artificial Sequence
<220> FEATURE:
<223> OTHER INFORMATION: corresponding amino acids around the CS in AIV
<220> FEATURE:
<221> NAME/KEY: MISC_FEATURE
<222> LOCATION: (1)..(13)

<400> SEQUENCE: 32

Pro Gln Arg Glu Ser Arg Arg Lys Lys Arg Gly Leu Phe
1 5 10

<210> SEQ ID NO 33
<211> LENGTH: 13
<212> TYPE: PRT
<213> ORGANISM: Artificial Sequence
<220> FEATURE:
<223> OTHER INFORMATION: corresponding amino acids around the CS in AIV
<220> FEATURE:
<221> NAME/KEY: MISC_FEATURE
<222> LOCATION: (1)..(13)

<400> SEQUENCE: 33

Pro Gln Arg Glu Arg Arg Arg Arg Lys Arg Gly Leu Phe
1 5 10

<210> SEQ ID NO 34
<211> LENGTH: 13
<212> TYPE: PRT
<213> ORGANISM: Artificial Sequence
<220> FEATURE:
<223> OTHER INFORMATION: corresponding amino acids around the CS in AIV
<220> FEATURE:
<221> NAME/KEY: MISC_FEATURE
<222> LOCATION: (1)..(13)

<400> SEQUENCE: 34

Pro Gln Arg Glu Arg Arg Arg Lys Lys Arg Gly Leu Phe
1 5 10

<210> SEQ ID NO 35
<211> LENGTH: 6
<212> TYPE: PRT
<213> ORGANISM: Artificial Sequence
<220> FEATURE:
<223> OTHER INFORMATION: corresponding amino acids in the CS site of AIV
<220> FEATURE:
<221> NAME/KEY: MISC_FEATURE
<222> LOCATION: (1)..(6)

<400> SEQUENCE: 35

Pro Gln Ile Glu Thr Arg
1 5

<210> SEQ ID NO 36
<211> LENGTH: 6
<212> TYPE: PRT
<213> ORGANISM: Artificial Sequence
<220> FEATURE:
<223> OTHER INFORMATION: corresponding amino acids in the CS site of AIV
<220> FEATURE:
<221> NAME/KEY: MISC_FEATURE
<222> LOCATION: (1)..(6)

<400> SEQUENCE: 36

Pro Gln Gly Glu Thr Arg
1 5

<210> SEQ ID NO 37

<211> LENGTH: 6
<212> TYPE: PRT
<213> ORGANISM: Artificial Sequence
<220> FEATURE:
<223> OTHER INFORMATION: corresponding amino acids in the CS site of AIV
<220> FEATURE:
<221> NAME/KEY: MISC_FEATURE
<222> LOCATION: (1)..(6)

<400> SEQUENCE: 37

Pro Gln Arg Glu Thr Arg
1               5

<210> SEQ ID NO 38
<211> LENGTH: 6
<212> TYPE: PRT
<213> ORGANISM: Artificial Sequence
<220> FEATURE:
<223> OTHER INFORMATION: corresponding amino acids in the CS site of AIV
<220> FEATURE:
<221> NAME/KEY: MISC_FEATURE
<222> LOCATION: (1)..(6)

<400> SEQUENCE: 38

Pro Gln Lys Glu Thr Arg
1               5

<210> SEQ ID NO 39
<211> LENGTH: 6
<212> TYPE: PRT
<213> ORGANISM: Artificial Sequence
<220> FEATURE:
<223> OTHER INFORMATION: corresponding amino acids in the CS site of AIV
<220> FEATURE:
<221> NAME/KEY: MISC_FEATURE
<222> LOCATION: (1)..(6)

<400> SEQUENCE: 39

Pro Gln Lys Glu Thr Lys
1               5

<210> SEQ ID NO 40
<211> LENGTH: 6
<212> TYPE: PRT
<213> ORGANISM: Artificial Sequence
<220> FEATURE:
<223> OTHER INFORMATION: corresponding amino acids in the CS site of AIV
<220> FEATURE:
<221> NAME/KEY: MISC_FEATURE
<222> LOCATION: (1)..(6)

<400> SEQUENCE: 40

Pro Lys Arg Glu Thr Arg
1               5

<210> SEQ ID NO 41
<211> LENGTH: 6
<212> TYPE: PRT
<213> ORGANISM: Artificial Sequence
<220> FEATURE:
<223> OTHER INFORMATION: corresponding amino acids in the CS site of AIV
<220> FEATURE:
<221> NAME/KEY: MISC_FEATURE
<222> LOCATION: (1)..(6)

<400> SEQUENCE: 41

Pro Gln Lys Glu Ala Arg
1               5

<210> SEQ ID NO 42
<211> LENGTH: 6
<212> TYPE: PRT
<213> ORGANISM: Artificial Sequence
<220> FEATURE:
<223> OTHER INFORMATION: corresponding amino acids in the CS site of AIV
<220> FEATURE:
<221> NAME/KEY: MISC_FEATURE
<222> LOCATION: (1)..(6)

<400> SEQUENCE: 42

Pro Gln Arg Ala Thr Arg
1               5

<210> SEQ ID NO 43
<211> LENGTH: 6
<212> TYPE: PRT
<213> ORGANISM: Artificial Sequence
<220> FEATURE:
<223> OTHER INFORMATION: corresponding amino acids in the CS site of AIV
<220> FEATURE:
<221> NAME/KEY: MISC_FEATURE
<222> LOCATION: (1)..(6)

<400> SEQUENCE: 43

Pro Gln Arg Ala Thr Lys
1               5

<210> SEQ ID NO 44
<211> LENGTH: 6
<212> TYPE: PRT
<213> ORGANISM: Artificial Sequence
<220> FEATURE:
<223> OTHER INFORMATION: corresponding amino acids in the CS site of AIV
<220> FEATURE:
<221> NAME/KEY: MISC_FEATURE
<222> LOCATION: (1)..(6)

<400> SEQUENCE: 44

Pro Gln Arg Thr Thr Arg
1               5

<210> SEQ ID NO 45
<211> LENGTH: 7
<212> TYPE: PRT
<213> ORGANISM: Artificial Sequence
<220> FEATURE:
<223> OTHER INFORMATION: corresponding amino acids in the CS site of AIV
<220> FEATURE:
<221> NAME/KEY: MISC_FEATURE
<222> LOCATION: (1)..(7)

<400> SEQUENCE: 45

Pro Glu Asn Pro Lys Pro Arg
1               5

<210> SEQ ID NO 46
<211> LENGTH: 6
<212> TYPE: PRT
<213> ORGANISM: Artificial Sequence
<220> FEATURE:
<223> OTHER INFORMATION: corresponding amino acids in the CS site of AIV
<220> FEATURE:
<221> NAME/KEY: MISC_FEATURE
<222> LOCATION: (1)..(6)

<400> SEQUENCE: 46

Arg Glu Lys Arg Gly Leu
1               5

<210> SEQ ID NO 47
<211> LENGTH: 6
<212> TYPE: PRT
<213> ORGANISM: Artificial Sequence
<220> FEATURE:
<223> OTHER INFORMATION: corresponding amino acids in the CS site of AIV
<220> FEATURE:
<221> NAME/KEY: MISC_FEATURE
<222> LOCATION: (1)..(6)

<400> SEQUENCE: 47

```
Pro Gln Arg Lys Thr Arg
1               5
```

<210> SEQ ID NO 48
<211> LENGTH: 6
<212> TYPE: PRT
<213> ORGANISM: Artificial Sequence
<220> FEATURE:
<223> OTHER INFORMATION: corresponding amino acids in the CS site of AIV
<220> FEATURE:
<221> NAME/KEY: MISC_FEATURE
<222> LOCATION: (1)..(6)

<400> SEQUENCE: 48

```
Pro Gln Arg Lys Lys Arg
1               5
```

<210> SEQ ID NO 49
<211> LENGTH: 6
<212> TYPE: PRT
<213> ORGANISM: Artificial Sequence
<220> FEATURE:
<223> OTHER INFORMATION: corresponding amino acids in the CS site of AIV
<220> FEATURE:
<221> NAME/KEY: MISC_FEATURE
<222> LOCATION: (1)..(6)

<400> SEQUENCE: 49

```
Pro Gln Arg Arg Lys Arg
1               5
```

<210> SEQ ID NO 50
<211> LENGTH: 6
<212> TYPE: PRT
<213> ORGANISM: Artificial Sequence
<220> FEATURE:
<223> OTHER INFORMATION: corresponding amino acids in the CS site of AIV
<220> FEATURE:
<221> NAME/KEY: MISC_FEATURE
<222> LOCATION: (1)..(6)

<400> SEQUENCE: 50

```
Pro Gln Lys Lys Lys Arg
1               5
```

<210> SEQ ID NO 51
<211> LENGTH: 6
<212> TYPE: PRT
<213> ORGANISM: Avian influenza virus
<220> FEATURE:
<221> NAME/KEY: MISC_FEATURE
<222> LOCATION: (1)..(6)
<223> OTHER INFORMATION: Xaa represents arginine (R) and lysine (K)

<400> SEQUENCE: 51

```
Pro Gln Xaa Gly Leu Phe
1               5
```

OLIGONUCLEOTIDE PROBES, KIT CONTAINING THE SAME AND METHOD FOR PATHOTYPING OF H5 AVIAN INFLUENZA VIRUSES

BACKGROUND OF THE INVENTION

1. Field of the Invention

The present invention relates to detection of infectious agents, more specifically, by using oligonucleotide probes, kit containing the same for rapid pathotyping of H5 avian influenza viruses.

2. Description of the Related Art

Avian Influenza virus (AIV) infects many animals such as humans, pigs, horses, marine mammals, and birds. Its natural reservoir is in aquatic birds, and in avian species most influenza virus infections cause mild localized infections of the respiratory and intestinal tract. While the majority of AIV subtypes are classified as low-pathogenicity avian influenza viruses (LPAIV), the H5 and H7 subtypes have the ability to mutate to high pathogenic avian influenza viruses (HPAIV). The HPAIV can have high pathogenic effect in poultry, with sudden outbreaks causing high mortality rates in affected poultry populations. In humans, the HPAIV cause a highly contagious acute respiratory disease that have resulted in epidemic and pandemic disease. Thus, it is of great importance to rapidly detect influenza viruses and promptly discriminate between LPAIV and HPAIV.

Reliable methods for pathotyping of AIV H5 viruses are based on determination of the intravenous pathogenicity index (IVPI) in specific pathogen free (SPF) chickens and on characterization of the hemagglutinin (HA) gene cleavage site (SC) by sequencing. The amino acid motif at the CS of the HA precursor protein of H5 viruses has been found to have a consistent format, $PQ^m$-$X^n$-*GLF (SEQ ID NO: 51) (Leijon et al., Journal of Clinical Microbiology, November 2011, p. 3860-3873) and a large number of Genbank nucleotide analysis ($^m$ Glutamine composes the vast majority, although other residues may be seen but few. X: all kinds of residues, in the present invention, it specifically represents arginine and lysine; n: the number of X. *Actual cleavage site at $HA_0$ by host proteases.) The number of basic amino acids (arginine and lysine) at X is an indicator of pathogenicity; in general, LPAIVs have one to three basic amino acids (n=1~3), and HPAIVs have four or more basic amino acids (n=4 or more).

Currently, there are a variety of techniques that can be used as a pathogenicity test for H5 avian influenza virus in biological samples, including PCR followed by nucleotides sequencing across the CS, real-time PCR, restriction enzyme cleavage pattern of reverse transcription PCR product and the like. However, those methods are time-consuming, labor-intensive, costly and highly complicated to perform. A microarray system, ArayTube, has been reported to pathotype AIV, however, the result interpretation needed the reader and was only limited to parts of H5 viruses, e.g. highly pathogenic H5/N1/Aisa clade 2.2.

Therefore, there remains a need for a lower cost, easier implement, more comprehensive and rapid approach with high sensitivity and specificity.

SUMMARY OF THE INVENTION

One aspect of the invention is to provide a probe selected from the group consisting of: SEQ ID NO: 1, SEQ ID NO: 2, SEQ ID NO: 3, SEQ ID NO: 4, SEQ ID NO: 5, SEQ ID NO: 6, SEQ ID NO: 7, SEQ ID NO: 8, SEQ ID NO: 9, SEQ ID NO: 10, SEQ ID NO: 11, SEQ ID NO: 12 and SEQ ID NO: 13.

Another aspect of the invention is to provide a kit for pathotyping of H5 avian influenza virus, comprising the probe selected from the group consisting of: SEQ ID NO: 1, SEQ ID NO: 2, SEQ ID NO: 3, SEQ ID NO: 4, SEQ ID NO: 5, SEQ ID NO: 6, SEQ ID NO: 7, SEQ ID NO: 8, SEQ ID NO: 9, SEQ ID NO: 10, SEQ ID NO: 11, SEQ ID NO: 12 and SEQ ID NO: 13.

Preferably, the probe is further added a tail composed of 19 T bases and is spotted to a microarray substrate.

Preferably, the kit further comprising an oligonucleotide of SEQ ID NO: 14 spotted on the microarray substrate as a positive control probe.

Still another aspect of the invention is to provide a method for pathotyping of H5 avian influenza virus in a sample, comprising: (a) obtaining a nucleic acid from the sample; (b) hybridizing the nucleic acid with a probe selected form the group consisting of: SEQ ID NO: 1, SEQ ID NO: 2, SEQ ID NO: 3, SEQ ID NO: 4, SEQ ID NO: 5, SEQ ID NO: 6, SEQ ID NO: 7, SEQ ID NO: 8, SEQ ID NO: 9, SEQ ID NO: 10, SEQ ID NO: 11, SEQ ID NO: 12 and SEQ ID NO: 13; and (c) pathotyping the sample as a low-pathogenic avian influenza virus (LPAIV) or highly pathogenic avian influenza virus (HPAIV) based on the hybridization result.

Preferably, the nucleic acid is obtained by extracting RNA from the sample, reverse transcribing the RNA into a DNA, and amplifying the DNA by a PCR reaction.

Preferably, a set of primers of SEQ ID NO: 15 and SEQ ID NO: 16 are used in the PCR reaction.

Preferably, the set of primers is 5' end-biotinylated.

Preferably, the nucleic acid further comprises a label. Preferably, the label is a fluorescent label, a chemiluminescent label, a colored dye label, a radioactive label, a radiopaque label, a protein including an enzyme, a peptide or a ligand.

Preferably, the H5 avian influenza virus is a highly pathogenic avian influenza viruses (HPAIV) when the nucleic acid is hybridized to the probe selected from SEQ ID NO: 12 and SEQ ID NO: 13 or the nucleic acid is hybridized only to the probe of SEQ ID NO: 1 or SEQ ID NO: 2, or both when all the probes are used.

Preferably, the H5 avian influenza virus is a low pathogenic avian influenza viruses (LPAIV) when the nucleic acid is hybridized to the probe selected from SEQ ID NO: 3, SEQ ID NO: 4, SEQ ID NO: 5, SEQ ID NO: 6, SEQ ID NO: 7, SEQ ID NO: 8 and SEQ ID NO: 9, SEQ ID NO: 10 and SEQ ID NO: 11.

BRIEF DESCRIPTION OF THE DRAWINGS

Non-limiting and non-exhaustive embodiments will be described in conjunction with the accompanying drawings. Understanding that these drawings depict only several embodiments in accordance with the disclosure and are, therefore, not to be intended to limit its scope, the disclosure will be described with specificity and detail through use of the accompanying drawings, in which.

DETAILED DESCRIPTION OF THE PREFERRED EMBODIMENTS

Figure 1:
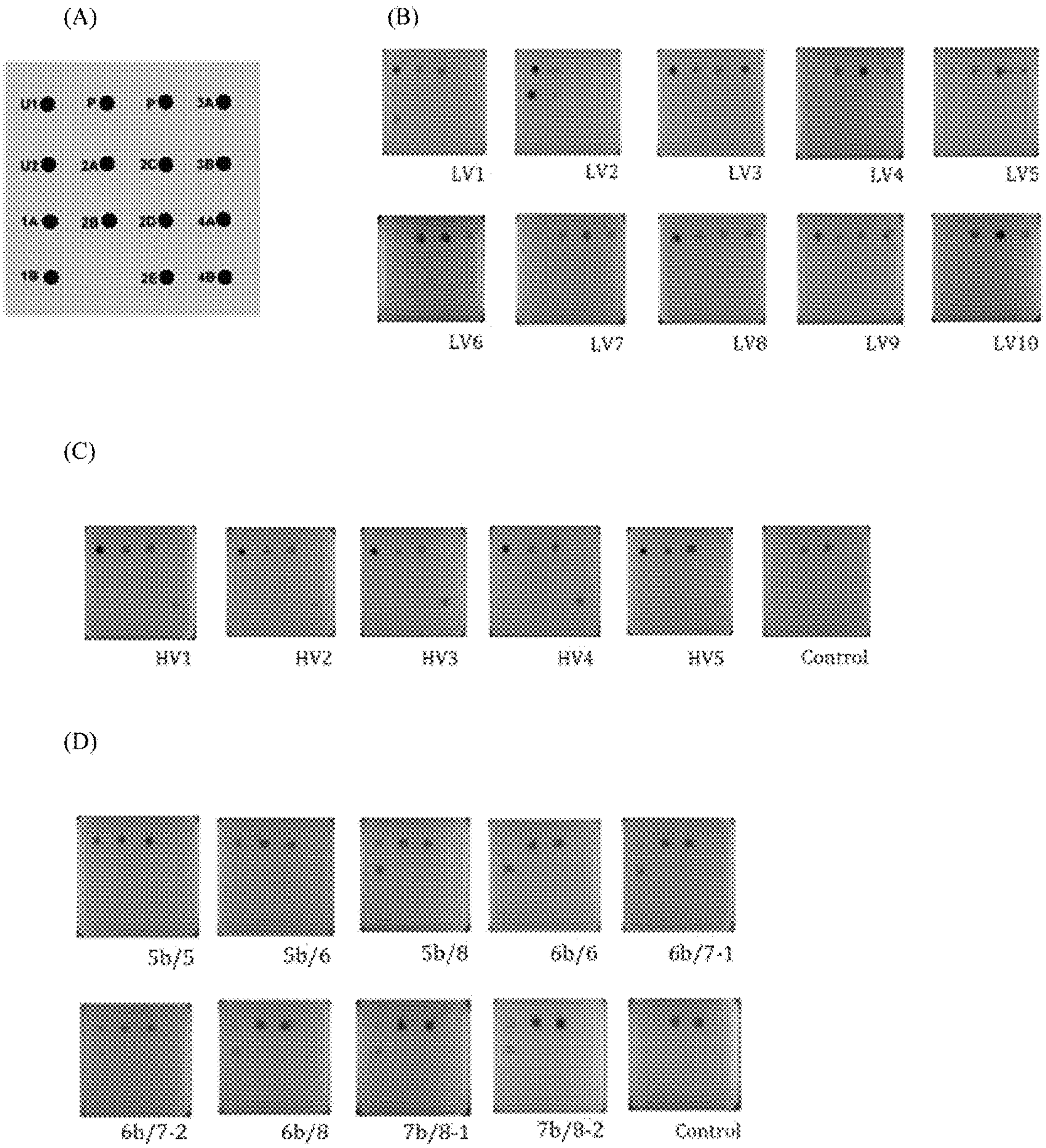
FIG. 1 shows detection and differentiation of AIVs using oligonucleotide microarrays. (A) Microarray map. The meaning of each probe and its detecting strains are shown in Table 3. P: positive control. The microarray detection results of LPAIVs, HPAIVs and the artificial oligonucleotides with five or more basic amino acids at the CS are shown on (B), (C), and (D), respectively. The denotation of each artificial oligonucleotide is shown in Table 2.

Hereinafter, illustrative embodiments and examples of the present disclosure will be described in detail with reference to the accompanying drawings so that inventive concept may be readily implemented by those skilled in the art.

However, it is to be noted that the present disclosure is not limited to the illustrative embodiments but can be realized in various other ways. In the drawings, certain parts not directly relevant to the description are omitted to enhance the clarity of the drawings, and like reference numerals denote like parts throughout the whole document.

Throughout the whole document, the term "comprises or includes" and/or "comprising or including" used in the document means that one or more other components, steps, operations, and/or the existence or addition of elements are not excluded in addition to the described components, steps, operations and/or elements. The terms "about or approximately" or "substantially" are intended to have meanings close to numerical values or ranges specified with an allowable error and intended to prevent accurate or absolute numerical values disclosed for understanding of the present invention from being illegally or unfairly used by any unconscionable third party. The terms "a" and "an" refer to one or to more than one (i.e., to at least one) of the grammatical object of the article.

The present invention provides oligonucleotide probes, kit containing the oligonucleotide probes and method for rapid pathotyping of H5 avian influenza viruses.

[Probes for Pathotyping of H5 Avian Influenza Viruses]

The present invention provides a probe selected from the group consisting of: SEQ ID NO: 1, SEQ ID NO: 2, SEQ ID NO: 3, SEQ ID NO: 4, SEQ ID NO: 5, SEQ ID NO: 6, SEQ ID NO: 7, SEQ ID NO: 8, SEQ ID NO: 9, SEQ ID NO: 10, SEQ ID NO: 11, SEQ ID NO: 12 and SEQ ID NO: 13 for pathotyping of H5 avian influenza viruses as a low-pathogenic avian influenza virus (LPAIV) or highly pathogenic avian influenza virus (HPAIV).

The term "pathotyping of H5 avian influenza viruses" used herein refers to detection of the number of X in the consistent format, $PQ^m$-$X^n$-*GLF (SEQ ID NO: 51), in H5 AIV amino acid motif at the CS of the HA precursor protein, wherein X represents basic amino acids (arginine (R) and lysine (K)). The term "low-pathogenic avian influenza virus (LPAIV)" used herein refers to H5 AIV has one to three basic amino acids at the above motioned amino acid motif, and the term "highly pathogenic avian influenza virus (HPAIV)" refers to H5 AIV has four or more basic amino acids at the above motioned amino acid motif.

In the present invention, the term "probe" includes at least 10 nucleotides of the nucleic acid sequences that are shown to encode specific amino acids or proteins. When referring to a probe, the term "specific for (a target sequence)" indicates that the probe hybridizes under stringent conditions substantially only to the target sequence in a given sample comprising the target sequence. The term "hybridization" used herein refers to the process wherein oligonucleotides and/or their analogs bind by hydrogen bonding, which includes Watson-Crick, Hoogsteen or reversed Hoogsteen hydrogen bonding, between complementary bases. Generally, nucleic acid consists of nitrogenous bases that are either pyrimidines (Cytosine (C), uracil (U), and thymine (T) or purines (adenine (A) and guanine (G)). These nitrogenous bases form hydrogen bonds consisting of a pyrimidine bonded to a purine, and the bonding of the pyrimidine to the purine is referred to as "base pairing." More specifically, A will bond to T or U, and G will bond to C. "Complementary" refers to the base pairing that occurs between two distinct nucleic acid sequences or two distinct regions of the same nucleic acid sequence. A person skilled in the art will appreciate that, depending on the context, the terms "binding", "hybridizing" or "hybridization" may be used interchangeably without giving rise to ambiguity. In the present invention, the probe may have the nucleotide sequence ambiguity. Where a nucleotide position is ambiguous and may be represented by one or more nucleotides, standardized symbols or letters, well known to a person skilled in the art, as given in the sequence listing of this application are used. Such symbols or letters, proposed by the International Union of Pure and Applied Chemistry which also corresponds to WIPO Standard ST.25 Appendix 2 Table 1, are as follows: M is A or C; R is A or G; W is A or T; S is C or G; Y is C or T; K is G or T; V is A or C or G; H is A or C or T; D is A or G or T; B is C or G or T; N is G or A or T or C.

In the present invention, the probes are used to detect and discriminate the basic amino acid number at the X of the $PQ^m$-$X^n$-*GLF (SEQ ID NO: 51) motif at the CS of the HA precursor protein of the H5 viruses. In the present invention, the probe selected from SEQ ID NO: 3 and SEQ ID NO: 4 detects LPAIV having 1 basic amino acid at X site (n=1); the probe selected from SEQ ID NO: 5, SEQ ID NO: 6, SEQ ID NO: 7, SEQ ID NO: 8 and SEQ ID NO: 9 detects LPAIV having 2 basic amino acids at X site (n=2); the probe selected from SEQ ID NO: 10 and SEQ ID NO: 11 detects LPAIV having 3 basic amino acids at X site (n=3); the probe selected from SEQ ID NO: 12 and SEQ ID NO: 13 detects HPAIV having 4 basic amino acids at X site (n=4). The probe, SEQ ID NO: 1 or SEQ ID NO: 2, is a universal probes, and all AIV H5 viruses can hybridize with either SEQ ID NO: 1 or SEQ ID NO: 2, or both. Thus, when all of the 13 probes (SEQ ID NO: 1 to SEQ ID NO: 13) are used, the sample of AIV H5 virus possess five or more basic amino acid (categorized as HPAIV) at the X (n=5) is hybridized either SEQ ID NO: 1 or SEQ ID NO: 2, or both, but is not hybridized with the probes of SEQ ID NO: 3 to SEQ ID NO: 13 which detects 1 to 4 basic amino acid(s) at X site (=1 to 4).

[Method for Rapid Pathotyping of H5 Avian Influenza Viruses]

According to the present invention, a method for pathotyping of H5 avian influenza virus in a sample is provided. The method comprises: (a) obtaining a nucleic acid from the sample; (b) hybridizing the nucleic acid with a probe selected form the group consisting of: SEQ ID NO: 1, SEQ ID NO: 2, SEQ ID NO: 3, SEQ ID NO: 4, SEQ ID NO: 5, SEQ ID NO: 6, SEQ ID NO: 7, SEQ ID NO: 8, SEQ ID NO: 9, SEQ ID NO: 10, SEQ ID NO: 11, SEQ ID NO: 12 and SEQ ID NO: 13; and (c) pathotyping the sample as a LPAIV or HPAIV based on the hybridization result.

According to the present invention, the term "sample" may be a biological sample, for example any sample collected from an individual suspected of carrying avian influenza virus subtype H5 or H5N1. The sample may be any sample that contains the virus from an infected individual, and includes tissue and fluid samples, for example, blood, serum, plasma, peripheral blood cells including lymphocytes and mononuclear cells, sputum, mucous, urine, feces, throat swab samples, dermal lesion swab samples, cerebrospinal fluids, pus, and tissue including spleen, kidney and liver.

According to the present invention, a nucleic acid from the sample is extracted from the sample for further evaluation. Preferably, a RNA from the sample is first extracted, and then reverse transcribed into a DNA (namely, cDNA), and the DNA is further amplified by a PCR reaction.

The term "RNA" refers to a sequence of two or more covalently bonded, naturally occurring or modified ribonucleotides. The RNA may be single stranded or double stranded. The term "DNA" refers to a sequence of two or more covalently bonded, naturally occurring or modified deoxyribonucleotides, including cDNA and synthetic (e. g., chemically synthesized) DNA, and may be double stranded or single stranded. By "reverse transcribed DNA" or "DNA reverse transcribed from" is meant complementary or copy DNA (cDNA) produced from an RNA template by the action of RNA-dependent DNA polymerase (reverse transcriptase). The template RNA for the reverse transcription reaction may be obtained from a sample using RNA extraction methods known in the art. RNA extraction kits are also commercially available, for example, RNeasy kits (Qiagen), and the availability and use of such kits will be known and understood by a skilled person.

Once the reverse transcription reaction is completed, the single-stranded DNA molecule can be used in the amplification reaction. The term "amplifying" or "amplification" refers to a reaction in which a nucleic acid molecule that is to be detected so as to pathotyping of H5 avian influenza virus as a HPAIV or a LPAIV. A suitable polymerase enzyme will be used to synthesize a new strand of a template nucleic acid to generate multiple copies.

The amplification step may be performed in the same reaction as the reverse transcription reaction, provided the conditions and reagents from the reverse transcription do not interfere with the amplification reaction. Alternatively, the reverse transcription product may be purified prior to being used as template in the amplification reaction.

According to the present invention, amplification is performed by a PCR amplification reaction. Thus, the amplification step may be performed with a DNA polymerase, for example, Taq polymerase, using standard methods and techniques that are known to a person skilled in the art. DNA polymerases for use in amplification of DNA molecules are commercially available. The amplification reaction is performed under conditions and with the necessary reagents, such as deoxynucleotides, buffer and relevant forward and reverse primers, so as to optimize the polymerization activity of the DNA polymerase enzyme.

The PCR amplification reaction involves a denaturation step, in which the reaction is heated to a temperature sufficient to denature the transcribed DNA strand and to prevent binding of the primers to either strand. The denaturation step is followed by an annealing step, in which the reaction temperature is ramped down to a temperature at which the primers can bind to the DNA strand. The final step is an extension step, in which the reaction is heated to a temperature that is optimal for extension of the primer by the DNA polymerase. These three steps are cycled through multiple times allowing for the production of the complementary strand of DNA that pairs with the reverse transcribed DNA and of the reverse transcribed strand by extension from the forward and reverse primer or primers respectively. In each successive round of the amplification reaction, more of each DNA strand is produced, which then may be used as template for the next cycle, resulting in amplification of the DNA product. A skilled person can readily determine the appropriate temperature for each segment of the amplification step and the desired number of cycles to be performed.

According to the present invention, the PCR procedure amplifies a conserved region of the CS of the HA precursor protein among HPAI and LPAI strains using specific primers.

As will be understood by a skilled person, a "primer" is a single-stranded DNA or RNA molecule of defined sequence that can base pair to a second DNA or RNA molecule that contains a complementary sequence (the target). The stability of the resulting hybrid molecule depends upon the extent of the base pairing that occurs, and is affected by parameters such as the degree of complementarity between the primer and target molecule and the degree of stringency of the hybridization conditions. The degree of hybridization stringency is affected by parameters such as the temperature, salt concentration, and concentration of organic molecules, such as formamide, and may be determined using methods that are known to those skilled in the art. Preferably, the primer may be modified with a label to allow for detection of the primer or a DNA product synthesized or extended from the primer. For example, the label may be a fluorescent label, a chemiluminescent label, a coloured dye label, a radioactive label, a radiopaque label, a protein including an enzyme, a peptide or a ligand for example biotin. Preferably, the primer is 5' end-biotinylated so that the yielded PCR products are biotinylated and are around 440 bp.

According to the present invention, since the PCR product (which is also known as "nucleic acid" as defined herein) is labeled when synthesized in the PCR procedure using labeled primers, the PCR product may be further detected by nucleic acid hybridization methods, single stranded conformational polymorphism (SSCP) analysis, restriction fragment polymorphism (RFLP) analysis, southern hybridization, northern hybridization, in situ hybridization, electrophoretic mobility shift assay (EMSA), nucleic acid microarrays, and other methods that are known to those skilled in the art.

According to the present invention, the labeled PCR product (nucleic acid) is hybridizing with a probe selected form the group consisting of: SEQ ID NO: 1, SEQ ID NO: 2, SEQ ID NO: 3, SEQ ID NO: 4, SEQ ID NO: 5, SEQ ID NO: 6, SEQ ID NO: 7, SEQ ID NO: 8, SEQ ID NO: 9, SEQ ID NO: 10, SEQ ID NO: 11, SEQ ID NO: 12 and SEQ ID NO: 13 for differentiating as a LPAIV or HPAIV based on the hybridization result. As described above, the sample contains HPAIV when the nucleic acid is hybridized to the probe selected from SEQ ID NO: 12 and SEQ ID NO: 13 or the nucleic acid is hybridized only to the probe of SEQ ID NO: 1 or SEQ ID NO: 2, or both when all the probes are used; the sample contains LPAIV when the nucleic acid is hybridized to the probe selected from SEQ ID NO: 3, SEQ ID NO: 4, SEQ ID NO: 5, SEQ ID NO: 6, SEQ ID NO: 7, SEQ ID NO: 8, SEQ ID NO: 9, SEQ ID NO: 10 and SEQ ID NO: 11.

The method for detection with the hybridization result based on different labeling of the PCR product is well-known in the art. Preferably, the PCR products are biotinylated so that the hybridization result is detected by the Biotin-Streptavidin System.

[Kit Containing the Oligonucleotide Probes]

The present invention also generally relates to a kit for pathotyping of H5 avian influenza virus in a biological sample or from biological material isolated and/or purified from a biological sample/

According to the present invention, a kit for pathotyping of H5 avian influenza virus, comprising the probe selected from the group consisting of: SEQ ID NO: 1, SEQ ID NO: 2, SEQ ID NO: 3, SEQ ID NO: 4, SEQ ID NO: 5, SEQ ID NO: 6, SEQ ID NO: 7, SEQ ID NO: 8, SEQ ID NO: 9, SEQ ID NO: 10, SEQ ID NO: 11, SEQ ID NO: 12 and SEQ ID NO: 13, is provided. Preferably, the probe may be immobilized on a solid support using standard methods, including chemical cross-linking, photocross-inking, or specific immobilization via a functional group on the probe. According to the present invention, a 19 T bases are added on each 5' end of probes and each probe is then spotted on the microarray polymer substrate using automatic spotting machine and immobilized by a UV crosslinker. The kit according to the present invention may optionally include a positive control probe, for example, a nuclei acid or at least portion thereof. Preferably, an oligonucleotide of SEQ ID NO: 14 is spotted on the microarray substrate as a positive control probe. The kit may further comprise information for use of the kit. It may be for example illustrative information provided by the manufacturer.

EXAMPLE

Hereinafter, the present disclosure will be specifically described with reference to examples and drawings. However, the present disclosure is not limited to the examples and the drawings.

[Origin of Influenza Virus Reference Strains and Field Samples]

The AIV reference strains used in the present invention are listed in Table 1. LV1-LV3 were field isolates originated from the Graduate Institute of Veterinary Medicine, National Taiwan University. LV4-LV10 and HV1-HV5 were obtained from the Epidemiology Division of the Animal Health Research Institute, Council of Agriculture, Tamsui, Taiwan.

TABLE 1

AIV strains used in the present invention

| Serial no. | Strain designation | Subtype | pathogenicity* | Genbank acc. no. |
|---|---|---|---|---|
| LV1 | A/duck/Yunlin/04 | H5N2 | LP | |
| LV2 | A/duck/Hong Kong/820/80 | H5N3 | LP | |
| LV3 | A/chicken/Taiwan/1209/03 | H5N2 | LP | AY573917 |
| LV4 | A/CK/Taiwan/1103/12 | H5N2 | LP | |
| LV5 | A/CK/Changhua/0102/10 | H5N2 | LP | |
| LV6 | A/CK/Chiayi/A1625/11 | H5N2 | LP | |
| LV7 | A/CK/Hsinchu/A1939/11 | H5N2 | LP | |
| LV8 | A/CK/Nantou/A2085/12 | H5N2 | LP | |
| LV9 | A/CK/Penghu/A2721/12 | H5N2 | LP | |
| LV10 | A/CK/Miaoli/1203/12 | H5N2 | HP | |
| HV1 | A/CK/Changhua/A1029/10 | H5N2 | HP | |
| HV2 | A/CK/Changhua/A1321/10 | H5N2 | HP | |
| HV3 | A/CK/Changhua/0101/12 | H5N2 | HP | KF193386 |
| HV4 | A/CK/Changhua/0302/12 | H5N2 | HP | |
| HV5 | A/CK/Yunlin/0502/12 | H5N2 | HP | |

*LP: low-pathogenicity; HP: high-pathogenicity

[RNA Extraction, Reverse Transcription and PCR]

Viruses were grown in the allantoic cavities of 9- to 10-day-old embryonated fowl eggs originating from a commercial SPF flock. Viral RNA was extracted from allantoic fluid using QIAamp Viral RBA kit (Qiagen, Valencia, Calif.). Field tissue samples were ground in liquid nitrogen and RNA was extracted us QIAamp RNeasy Mini Kit (Qiagen, Hilden, Germany). The reverse transcription was then performed with uni12 primer (Hoffmann B, Harder T, Starick E, et al.: 2007, J Clin Microbiol 45: 600-603) using Transcriptor High Fidelity cDNA Synthesis Kit (Roche, Mannheim, Germany) according to the manufacture's instructions. Specific H5 primer pair (H5f/H5r) flanking the CS was designed from conserved regions among HPAI and LPAI strains obtained from the GenBank data. The primer H5f (5'-ATWGCTCCNGAATATGCATWWAARA-3' (SEQ ID NO: 15)) and H5r (5'-TCRAAYTGARTGTTCATTTTRTCAATG-3' (SEQ ID NO: 16)) were 5' end-biotinylated and yielded products were around 440 bp. The PCR was carried out in a reaction volume of 50 μl containing 5 μl of template, 5 μl of each primer (10 μM), 5 μl of 10×PCR buffer, 4 μl of each dNTP (2.5 mM), 0.3 μl (5 U/μl) of GenTaq Plus DNA polymerase (GeneMark, Taichung, Taiwan). The thermal profile for amplification was 94° C. for 3 min, 40×(94° C. for 30 s, 50° C. for 30 s, and 72° C. for 40 s), 72° C. for 7 min. Ten μl PCR products were separated in 1.5% agarose gels (Gibco, Grand Island, N.Y.), run in 0.5×TAE buffer with 0.5 μg/ml ethidium bromide (Gibco, Grand Island, N.Y.) at 100 V for 40 min, and visualized under UV light.

[Cloning and Sequencing]

The PCR products were purified by PCR clean-up kit (GeneMark, Taichung, Taiwan) and cloned into plasmid vectors using pGEM-T EASY Vector System (Promega, Madison, Wis.) following the manufacturer's instructions. The plasmids were then transformed into competent cells (ARROWTEC, Taipei, Taiwan) which were further cultured on the LB agar (BD Difco, Sparks, Md.). The colonies with successful inserts were confirmed by PCR using plasmid T7 and SP6 primers and then amplified in the LB broth (BD Difco, Sparks, Md.). Plasmid DNA was extracted using Miniprep Purification Kit (Protech Co., Taipei, Taiwan) and the inserts were further sequenced by means of commercial service (Protech Co., Taipei, Taiwan). The $HA_0$ nucleotide sequence spanning the cleavage site of each reference virus and the test sample was then attained.

[Artificial Oligonucleotides]

Because of the extensive nucleotide variety at the CS and the viral territorial characteristic of the H5 AIVs, no virus isolates with five or more basic amino acids at the X of the $PQ^m$-$X^n$-*GLF (SEQ ID NO: 51) motif were available in Taiwan. A comprehensive alignment and analysis of all AIV H5 sequences from Genbank were made. Nine representative sequences which possess five or more basic amino acids at the X and encompass the CS diversity were selected. Oligonucleotides spanning the CS region with 114-122 bases long of the nine representative sequences were synthesized artificially (Table 2). These artificial oligonucleotides were amplified using their own primers in accordance with the sequences located at the two ends. The amplicons were verified on agarose gel and were further tested on the microarrays to simulate those genuine viruses.

TABLE 2

Artificial oligonucleotides which possess five or more corresponding basic amino acids at the X of the PQ-$X^n$-GLF (SEQ ID NO: 51) motif.

| Artificial oligo-nucleotide[a] | Sequence (5'-3')[b] | Corresponding amino acids around the CS[c] | Basic amino acid number at X[c] | Genbank acc.no. |
|---|---|---|---|---|
| 5b/5 | CCCCTTACCATTGGAGAGTGTCCCAAATATGTCAAATCAAATAAACTGGTCC<br>TTGCAACAGGACCGAGGAACGTGCCTCAAAGAAGAAAAAAAAGAGGTCTGTT<br>TGGAGCAAAAGC<br>(SEQ ID NO: 17) | PQ-RRKKR-GLF<br>(SEQ ID NO: 26) | 5 | AB241613 |
| 5b/6 | TCCTTTTACTATTGGGGAGTGCCCCAAGTATGTCAAATCGAAAAAACTAGTT<br>CTTGCAACAGGGCTAAGAAACGTACCCCAAAGAAAAAGAAAAACAAGAGGCC<br>TATTTGGAGCAATAGC<br>(SEQ ID NO: 18) | PQ-RKRKTR-GLF<br>(SEQ ID NO: 27) | 5 | AB558474 |
| 5b/8 | CTCTCACCATCGGGGAATGCCCCAAATATGTGAAATCAAACAGATTAGTCCT<br>CGCGACTGGACTCAGAAATGCCCCCCAAATAGAGGGAAGAAGAAGAAAAAGA<br>GGACTATTTGGAGCCATA<br>(SEQ ID NO: 19) | PQ-IEGRRRKR-GLF<br>(SEQ ID NO: 28) | 5 | HM583608 |
| 6b/6 | CTCTCACCATTGGGGAATGCCCCAGATACGTGAAATCAGATAGATTAGTCCT<br>TGCGACTGGACTCAGGAATGTCCCTCAAAGAAGAAGAAAAAAAAGAGGACTA<br>TTTGGGGCTATAGC<br>(SEQ ID NO: 20) | PQ-RRRKKR-GLF<br>(SEQ ID NO: 29) | 6 | AJ305306 |
| 6b/7-1 | CTCTCACCATCGGGGAATGCCCCAAATATGTGAAATCAAACAGATTAGTCCT<br>TGCGACTGGGCTCAGAAATAGCCCTCAAAGAGAGAGAAGAAAAAAGAGAGGA<br>TTATTTGGAGCTATAGC<br>(SEQ ID NO: 21) | PQ-RERRKKR-GLF<br>(SEQ ID NO: 30) | 6 | AM183676 |
| 6b/7-2 | CTCTCACCATCGGGGAATGCCCCAAATATGTGAAATCAAACAAATTGGTCCT<br>TGCGACTGGGCTCAGAAATAGTCCTCTAAGAGAAAGAAGAAGAAAAAGAGGA<br>CTATTTGGAGCTATAGC<br>(SEQ ID NO: 22) | PL-RERRRKR-GLF<br>(SEQ ID NO: 31) | 6 | EF419243 |
| 6b/8 | CTCTCACCATCGGGGAATGCCCCAAATATGTGAAATCAAACAGATTAGTCCT<br>TGCAACAGGACTCAGAAACAGCCCTCAAAGAGAGAGCAGAAGAAAAAAGAGA<br>GGACTATTTGGAGCTATAGC<br>(SEQ ID NO: 23) | PQ-RESRRKKR-GLF<br>(SEQ ID NO: 32) | 6 | CY091963 |
| 7b/8-1 | CTCTCACCATCGGAGAATGTCCCAAATATGTGAAATCAAACAAATTAGTCCT<br>TGCGACTGGGCTCAGAAATAGTCCTCAAAGAGAGAGAAGAAGAAGAAAAAAGA<br>GGACTGTTTGGAGCTATAGC<br>(SEQ ID NO: 24) | PQ-RERRRRKR-GLF<br>(SEQ ID NO: 33) | 7 | KF169907 |
| 7b/8-2 | CTCTCACCATCGGGGAATGCCCCAAATATGTGAAATCAAACAGATTAGTCCT<br>TGCGACTGGGCTCAGAAATAGCCCTCAAAGAGAGAGAAGAAGAAAAAAGAGA<br>GGACTATTTGGAGCTATAGC<br>(SEQ ID NO: 25) | PQ-RERRRKKR-GLF<br>(SEQ ID NO: 34) | 7 | CY091949 |

[a]The symbol n'b/n means there are n' basic amino acids among the total n amino acids at X.
[b]The nucleotide bases corresponding to PQ-$X^n$-GLF (SEQ ID NO: 51) amino acid motif at CS are underlined.
[c]Basic amino acid at the X is marked with a bottom line and the number is counted.

[Probe Design]

The universal probes targeting all AIV H5 subtypes were designed from the conserved sequences of the HA gene located within the H5f/H5r amplicons. All AIV H5 viruses can hybridize with either universal probe U1 or U2, or both. Probes for differentiating LPAIVs and HPAIVs were designed based on the basic amino acid number at the X of the PQ$^m$-$X^n$-*GLF (SEQ ID NO: 51) motif of the CS. Eleven differentiating probes comprehensively encompassing the highly variable CS region of the H5 viruses were designed. The designs of all probes as well as the primer pair H5f/H5r were derived from the alignment and analyses of the nucleotide sequences retrieved from the enormous GenBank data, and conducted by the MegAlign program (DNASTAR, Madison, Wis., US). The probe sequences are listed in Table 3.

TABLE 3

Probes used to detect and discriminate the basic amino acid number at the X of the PQ-$X^n$-GLF (SEQ ID NO: 51) motif at CS of H5 viruses.

| Probe | Sequence (5'-3') | Corresponding amino acids† | Basic amino acid number at X[b] | AIV strains used in this study |
|---|---|---|---|---|
| U1[a] | GAGTGYCCMAARTAYGTSAAAT<br>(SEQ ID NO: 1) | | | |

TABLE 3-continued

Probes used to detect and discriminate the basic amino acid number at the X of the PQ-$X^n$-GLF (SEQ ID NO: 51) motif at CS of H5 viruses.

| Probe | Sequence (5'-3') | Corresponding amino acids† | Basic amino acid number at X[b] | AIV strains used in this study |
|---|---|---|---|---|
| U2[a] | GAATGYCCCARATAYGTGAAAT (SEQ ID NO: 2) | | | |
| 1A | CCY CAR ATA GAR ACA AGR (SEQ ID NO: 3) | PQ-IETR (SEQ ID NO: 35) | 1 | LV1 |
| 1B | CCY CAR GGA GAR ACA AGR (SEQ ID NO: 4) | PQ-GETR (SEQ ID NO: 36) | 1 | |
| 2A | CCY CAR AGA GAR ACR AGA (SEQ ID NO: 5) | PQ-RETR (SEQ ID NO: 37) | 2 | LV2 |
| 2B | CCY CAA AAR GAA ACA ARA (SEQ ID NO: 6) | PQ-KETR (SEQ ID NO: 38), PQ-KETK (SEQ ID NO: 39) | 2 | |
| 2C | CCY MAA ARA GAA RCA AGA (SEQ ID NO: 7) | PK-RETR (SEQ ID NO: 40), PQ-KEAR (SEQ ID NO: 41) | 2 | |
| 2D | CCY CAA AGA RCC ACA ARA (SEQ ID NO: 8) | PQ-RATR (SEQ ID NO: 42), PQ-RATK (SEQ ID NO: 43), PQ-RTTR (SEQ ID NO: 44) | 2 | |
| 2E | CCA GAG AAT CCA AAG CCC (SEQ ID NO: 9) | PE-NPKPR (SEQ ID NO: 45) | 2 | |
| 3A | MGA GAA AAA AGA GGM CTA (SEQ ID NO: 10) | REKR-GL (SEQ ID NO: 46) | 3 | LV3-LV10 |
| 3B | CCY CAA AGA AAA ACA AGA (SEQ ID NO: 11) | PQ-RKTR (SEQ ID NO: 47) | 3 | |
| 4A | CCY CAA AGR ARR AAA AGA (SEQ ID NO: 12) | PQ-RKKR (SEQ ID NO: 48) PQ-RRKR (SEQ ID NO: 49) | 4 | HV1-HV3 HV4-HV5 |
| 4B | CCY CAG AAG AAR AAG AGA (SEQ ID NO: 13) | PQ-KKKR (SEQ ID NO: 50) | 4 | |

[a]Universal probes. All AIV H5 viruses can hybridize with either probe U1 or U2, or both.
[b]Basic amino acid at the X is marked with a bottom line and the number is counted.

[Oligonucleotide Microarray Preparation and Hybridization Reaction]

A tail composed of 19 T bases was added on each 5' end of oligonucleotide probe, including the positive control probe (an oligonucleotide from capsid protein VP 1 of human enterovirus 71 gene, 5'-ATGAAGCATGTCAGGGCTTGGATACCTCG-3' (SEQ ID NO: 14)). Fifteen mM of each probe was then spotted to each specific position on the microarray polymer substrate using an automatic spotting machine (DR. Easy spotter, Maio-Li, Taiwan), and immobilized by a UV crosslinker (STRATAGENE UV Stratalinker 1800, Santa Clara, USA) with 0.24 J. The hybridization reaction between each DNA template and probe was carried out with DR. Chip DIY Kit (DR. Chip Biotech, Maio-Li, Taiwan). The procedures followed the manual and are briefly described below. The PCR product was denatured at 95° C. for 10 min, and cooled in an ice bath for 2 min. To the microarray chamber was added 200 ml of Hybridization Buffer (containing the 50 end-biotinylated oligonucleotide complementary to the sequence of positive control probe) and 1 μl of denatured PCR product, incubated at 47° C. with vibration for 1 hr, and washed three times with Wash Buffer. The blocking reaction was then performed by mixing 0.2 ml of Strep-AP (Streptavidin conjugate alkaline phosphatase) and 200 ml of Blocking Reagent at room temperature for 30 min, and washing three times with Wash Buffer. The colorimetric reaction was then implemented by adding 4 ml of NBT/BCIP and 196 ml of Detection Buffer in the chamber, developing in the dark at room temperature for 20 min, and washing twice with distilled water. The hybridization result as shown in FIG. 1 was indicated as the developed pattern on the microarray, which was read directly with the naked eyes.

As FIG. 1 shows, fifteen H5 AIVs, including ten LPAIVs and five HPAIVs (Table1) were tested using oligonucleotide microarrays following the PCR. All viruses were unambiguously detected and pathotyped, and no cross-reactions were found (FIGS. 1 B and C). The microarray results were completely concordant with the results of direct sequence analysis of the H5 gene spanning the CS region (Table 3).

The microarray detection results of artificial oligonucleotides are shown in FIG. 1 D. The nine representative AIV H5 oligonucleotides which possess five or more basic amino acids at the X displayed positive at the universal probe dots, either at U1 or U2, or both. No cross-reaction with other probes which detected one to four basic amino acids at X was found. This demonstrated good probe specificity of the probes. The total designed 13 probes could successfully differentiate the number of basic amino acids and recognize the HPAIVs which possess five or more basic amino acids at the X of the CS $PQ^m$-$X^n$-*GLF (SEQ ID NO: 51) motif. The hybridization signals on microarrays indicated by colorimetry in the present invention made the results clearly identifiable using the naked eyes, that is, no additional imaging equipment was needed here. This finding shows that the simultaneous detection and pathotyping of AIV H5 viruses can be inexpensively and easily achieved using oligonucleotide microarrays.

[Detection Limit]

The plasmid DNA with successful insert was extracted and quantified with a spectrophotometer (WPA UV1101, Biochrom Ltd, Cambridge, UK). The copy numbers of the DNA were calculated and the DNA was then diluted serially in TE buffer. The sensitivity of agarose gel and oligonucleotide microarray was investigated and compared by testing 10-fold serial dilations of DNA ($10^7$ to $10^0$ copies) originating from the AIV reference strains.

Figure 2:
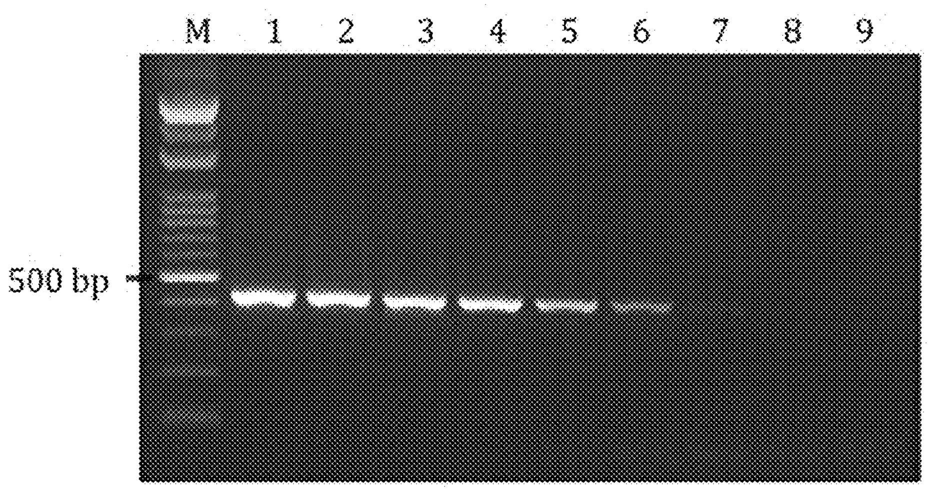
FIG. 2 shows detection limit test using A/CK/Hsinchu/A1939/11 (LV7) as an example. (A) Cloned plasmid was serial diluted (indicated as copy numbers) and PCR-amplified using primer pair H5f/H5r. M: 100 bp ladder marker; 1: $4.6\times10^7$ copies/μL; 2: $4.6\times10^6$ copies/μL; 3: $4.6\times10^5$ copies/μL; 4: $4.6\times10^4$ copies/μL; 5: $4.6\times10^3$ copies/μL; 6: $4.6\times10^2$ copies/μL; 7: $4.6\times10^1$ copies/μL; 8: $4.6\times10^0$ copies/μL; 9: negative control. (B) The corresponding results on the oligonucleotide microarrays.
Figure 2:
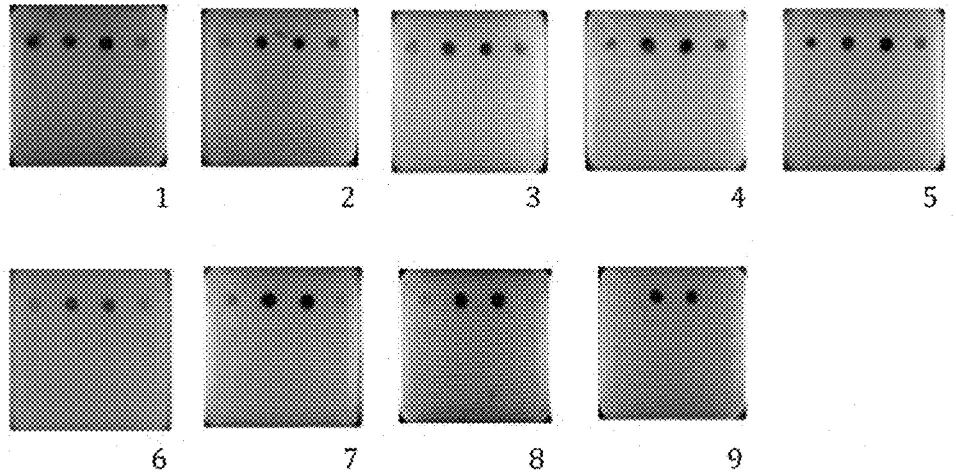

The sensitivity comparison test between the agarose gel assay and oligonucleotide microarray using A/CK/Hsinchu/A1939/11 (LV7) as an example is shown in FIG. 2. The results showed that DNA below $4.6\times10^2$ copies/μL could not be seen on agarose gel. However, DNA with 4.6 copies/μL could still be read on the microarrays. This indicated that the sensitivity of oligonucleotide microarray sensitivity was about 100 times higher than that of the agarose gel assay.

The oligonucleotide microarray assay described in the present invention offers a simple, rapid and accurate approach to discriminate between LPAIVs and HPAIVs. This method provides new opportunities for avian influenza surveillance and diagnostics and may be particularly attractive for large-scale screening of suspected AIV H5 viruses during outbreaks for regional diagnostic laboratories.

While example embodiments have been disclosed herein, it should be understood that other variations may be possible. Such variations are not to be regarded as a departure from the spirit and scope of example embodiments of the present application, and all such modifications as would be obvious to one skilled in the art are intended to be included within the scope of the following claims.

What is claimed is:

1. A microarray for detecting H5 avian influenza virus and pathotyping the detected H5 avian influenza virus as a low-pathogenic avian influenza virus (LPAIV) or a highly-pathogenic avian influenza virus (HPAIV), comprising the following probes (i) to (v):

(i) at least one probe comprising the nucleotide sequence of 5'-GAATGYCCCARATAYGTGAAAT-3' (SEQ ID NO: 2);

(ii) at least one probe comprising the nucleotide sequence of 5'-CCYCARATAGARACAAGR-3' (SEQ ID NO: 3);

(iii) at least one probe comprising the nucleotide sequence of 5'-CCYCAR AGAGARACRAGA-3' (SEQ ID NO: 5);

(iv) at least one probe comprising the nucleotide sequence of 5'-MGAGAAAAAAGAGGMCTA-3' (SEQ ID NO: 10); and (v) at least one probe comprising the nucleotide sequence of 5'-CCYCAAAGRARRAAAAGA-3' (SEQ ID NO: 12);

wherein each of probes (i) to (v) have a tail composed of 19T bases added on their 5' end; and wherein Y is C or T, M is A or C, R is A or G, and S is C or G.

2. A kit comprising the microarray defined in claim 1.

3. The microarray of claim 1, further comprising a positive control probe comprising the nucleotide sequence of SEQ ID NO: 14; wherein the positive control probe has a tail composed of 19T bases added on its 5' end.

4. The microarray of claim 1, wherein the microarray further comprises one or more probes of 5'-GAGTGYCCMAARTAYGTSAAAT-3' (SEQ ID NO: 1), 5'-CCYCARGGAGARACAAGR-3' (SEQ ID NO: 4), 5'-CCYCAAAARGAAACAARA-3' (SEQ ID NO: 6), 5'-CCYMAAARAGAARCAAGA-3' (SEQ ID NO: 7), 5'-CCYCAAAGARCCACAARA-3' (SEQ ID NO: 8), 5'-CCAGAGAATCCAAAGCCC-3' (SEQ ID NO: 9), 5'-CCYCAAAGAAAAACAAGA-3 '(SEQ ID NO: 11) and 5'-CCYCAGAAGAARAAGAGA-3' (SEQ ID NO: 13), wherein each of the one or more probes has a tail composed of 19T bases added on its 5' end; and wherein Y is C or T, M is A or C, R is A or G, and S is C or G.

5. A method for detecting H5 avian influenza virus and pathotyping the detected H5 avian influenza virus as a low-pathogenic avian influenza virus (LPAIV) or a highly-pathogenic avian influenza virus (HPAIV) in a biological sample comprising:

(a) obtaining nucleic acid from the biological sample;

(b) contacting the nucleic acid with the microarray of claim 1; and (c) detecting H5 avian influenza and pathotyping it as HPAIV when the nucleic acid hybridizes to the at least one probe of (v) or to only the at least one probe of (i); or detecting H5 avian influenza and pathotyping it as LPAIV when the nucleic acid hybridizes to the at least one probe of (ii), (iii), or (iv).

6. The method of claim 5, wherein the nucleic acid obtained from the biological sample is RNA and the RNA is reverse transcribed into DNA and amplified by a PCR reaction prior to contacting.

7. The method of claim 6, wherein primers SEQ ID NO: 15 and SEQ ID NO: 16 are used in the PCR reaction.

8. The method of claim 7, wherein the primers are 5' end-biotinylated.

9. The method of claim 5, wherein the nucleic acid further comprises a label.

10. The method of claim 9, wherein the label is a fluorescent label, a chemiluminescent label, a colored dye label, a radioactive label, a radiopaque label, a protein including an enzyme, a peptide or a ligand.

* * * * *